(12) United States Patent
Kotcherlakota et al.

(10) Patent No.: US 10,806,715 B2
(45) Date of Patent: Oct. 20, 2020

(54) GOLD NANOPARTICLE BASED FORMULATION FOR USE IN CANCER THERAPY

(71) Applicant: COUNCIL OF SCIENTIFIC & INDUSTRIAL RESEARCH, New Delhi (IN)

(72) Inventors: Rajesh Kotcherlakota, Hyderabad (IN); Sudip Mukherjee, Hyderabad (IN); Chitta Ranjan Patra, Hyderabad (IN); Vijaya Gopal, Hyderabad (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 16/344,519

(22) PCT Filed: Oct. 23, 2017

(86) PCT No.: PCT/IN2017/050488
§ 371 (c)(1),
(2) Date: Apr. 24, 2019

(87) PCT Pub. No.: WO2018/078648
PCT Pub. Date: May 3, 2018

(65) Prior Publication Data
US 2019/0240186 A1 Aug. 8, 2019

(30) Foreign Application Priority Data
Oct. 25, 2016 (IN) .............................. 201611036499

(51) Int. Cl.
| | | |
|---|---|---|
| *A61K 48/00* | (2006.01) | |
| *C07H 21/04* | (2006.01) | |
| *A61K 31/351* | (2006.01) | |
| *A61K 47/62* | (2017.01) | |
| *A61K 47/69* | (2017.01) | |
| *A61K 31/713* | (2006.01) | |
| *A61K 31/24* | (2006.01) | |
| *A61K 31/704* | (2006.01) | |
| *A61K 33/24* | (2019.01) | |
| *A61P 35/00* | (2006.01) | |
| *A61K 31/7105* | (2006.01) | |
| *A61K 33/243* | (2019.01) | |
| *A61K 9/00* | (2006.01) | |
| *A61K 31/519* | (2006.01) | |

(52) U.S. Cl.
CPC ............ *A61K 31/351* (2013.01); *A61K 31/24* (2013.01); *A61K 31/704* (2013.01); *A61K 31/713* (2013.01); *A61K 31/7105* (2013.01); *A61K 33/24* (2013.01); *A61K 47/62* (2017.08); *A61K 47/6923* (2017.08); *A61K 47/6929* (2017.08); *A61P 35/00* (2018.01); *A61K 9/0019* (2013.01); *A61K 31/519* (2013.01); *A61K 33/243* (2019.01)

(58) Field of Classification Search
CPC ..................................................... A61K 31/713
See application file for complete search history.

(56) References Cited

U.S. PATENT DOCUMENTS

| | | | |
|---|---|---|---|
| 2009/0148535 A1 | 6/2009 | Bamdad | |
| 2010/0291681 A1* | 11/2010 | Khvorova | ............ A61K 31/713 435/440 |
| 2012/0282245 A1 | 11/2012 | Lukashev et al. | |
| 2013/0216600 A1 | 8/2013 | Da Sliva Ferreira et al. | |
| 2014/0141986 A1 | 5/2014 | Spetzler et al. | |
| 2015/0044694 A1 | 2/2015 | Wu et al. | |
| 2016/0287723 A1 | 10/2016 | Cheng et al. | |

FOREIGN PATENT DOCUMENTS

| | | |
|---|---|---|
| WO | WO2012058627 A2 | 5/2012 |
| WO | WO2015074762 A1 | 5/2015 |
| WO | WO2016004043 A1 | 1/2016 |
| WO | WO2017136652 A1 | 8/2017 |
| WO | WO2018078648 A2 | 5/2018 |

OTHER PUBLICATIONS

Singhana et al. (AAPS PharmSciTech. Jun. 2014;15(3):741-52).*
Alexis et al., "HER-2 Targeted Nanoparticle-Athbody Bioconjugates for Cancer Therapy", ChemMedChem, 3(12): 2008, pp. 1839-1843.
Bradford, "A Rapid and Sensitive Method for the Quantitation of Microgram Quantities of Protein Utilizing the Principle of Protein-Dye Binding", Analytical Biochemistry, vol. 72, 1976, pp. 248-254.
Daniel et al., "Gold Nanoparticles: Assembly, Supramolecular Chemistry, Quantum-Size-Related Properties, and Applications toward Biology, Catalysis, and Nanotechnology", Chem. Rev., vol. 104, 2004, pp. 293-346.

(Continued)

*Primary Examiner* — Amy H Bowman
(74) *Attorney, Agent, or Firm* — Dinsmore & Shohl LLP

(57) ABSTRACT

The current invention relates to development of new formulation containing gold nanoparticles (AuNPs) with bi-functional recombinant fusion proteins TRAF(C) for the delivery of anticancer drugs and nucleic acids to HER2+ cancers. Using the combinatorial approach, we designed gold nanoparticle-based targeted drug delivery system (TDDS) or (Au-TR-DX-si) by combining AuNPs with bi-functional recombinant fusion protein TRAF(C) (TR), doxorubicin (DX) and siRNA (si). The recombinant protein based gold nanoparticles formulations are stable and homogenous as revealed by several physicochemical studies. In addition, the engineered fusion protein TRAF (C) has the ability to target selectively to HER2+ receptors overexpressed in ovarian cancer cells (SK-OV-3).

10 Claims, 4 Drawing Sheets

Figure 1:
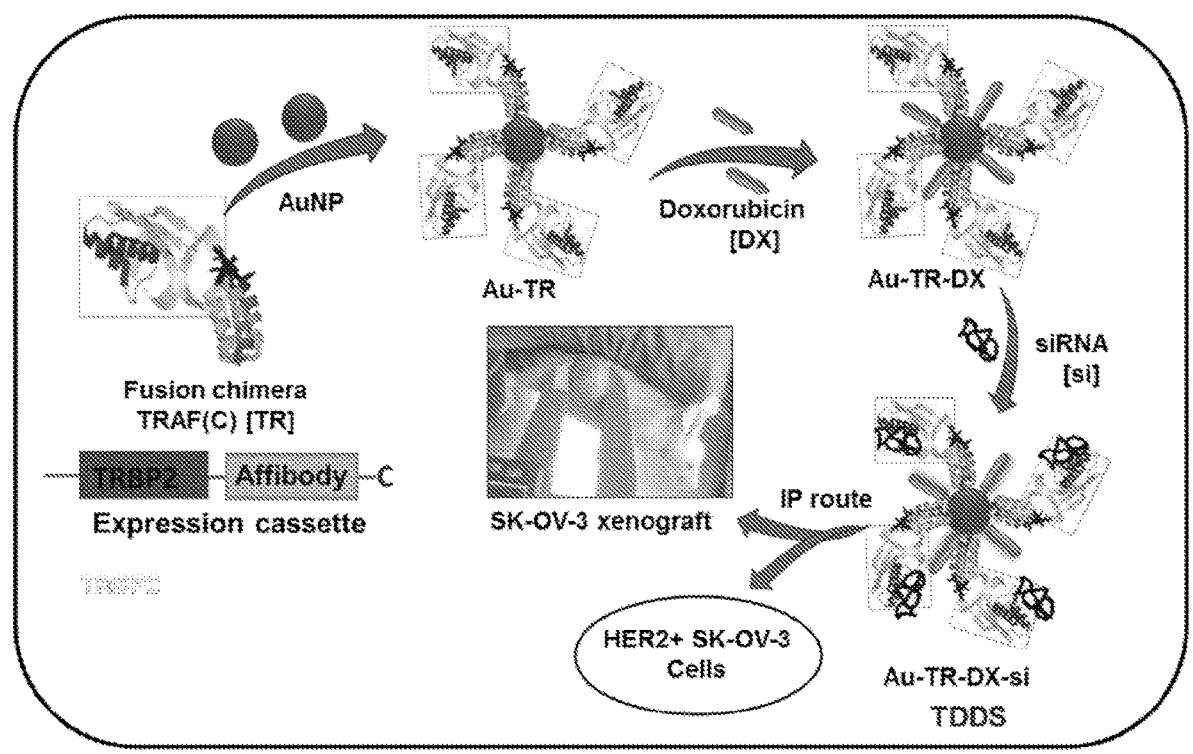

Specification includes a Sequence Listing.

(56) References Cited

OTHER PUBLICATIONS

Dar et al., "Conformation-dependent binding and tumor-targeted delivery of siRNA by a designed TRBP2: Affibody fusion protein", Nanomedicine: Nanotechnology, Biology, and Medicine, vol. 11, 2015, pp. 1455-1466.

Geng et al., "Structure-based Design of Peptides with High Affinity and Specificity to HER2 Positive Tumors", Theranostics, vol. 5, Issue 10, 2015, pp. 1154-.

Govindarajan et al., "Targeting human epidermal growth factor receptor 2 by a cell-penetrating peptide-affibody bioconjugate", Biomaterials, vol. 33, 2012, pp. 2570-2582.

Hanahan et a., "The Hallmark of Cancer", cell, vol. 100, Jan. 7, 2000, pp. 57-70.

Konstantinopoulos et al., "Gene-expression profiling in epithelial ovarian cancer", Nature Clinical Practice Oncology, VI. 5, No. 10, 2008, pp. 577-587.

Laemmli et al., "Cleavage of Structural Proteins during the Assembly of the Head of Bacteriophage T4", Nature, vol. 227, 1970, pp. 680-685.

Li et al., "Molecular-targeted agents combination therapy for cancer: Developments and potentials", International Journal of Cancer, vol. 134, 2014, pp. 1257-1269.

Menon, "Sensitivity and specificity of multimodal and ultrasound screening for ovarian cancer, and stage distribution of detected cancers: results of the prevalence screen of the UK Collaborative Trial of Ovarian Cancer Screening (UKCTOCS)", The Lancet Oncology, vol. 10, 2009, pp. 327-340.

Paciotti et al., "Colloidal Gold Nanoparticles: A Novel Nanoparticle Platform for Developing Multifunctional Tumor-Targeted Drug Delivery Vectors", Drug Development Research, vol. 67, 2006, pp. 47-54.

Patra et al., "Fabrication of gold nanoparticles for targeted therapy in pancreatic cancer", Advanced Drug Delivery Reviews, vol. 62, 2010, pp. 346-361.

Peer et al., "Nanocarriers as an emerging platform for cancer therapy", Nature Nanotechnology, vol. 2, 2007, pp. 751-760.

Siegel et al., "Cancer Statistics, 2015", CA Cancer J Clin, vol. 65, 2015, pp. 5-29.

Srinivas et al., "A long-lasting dendritic cell DNA vaccination system using lysinylated amphiphiles with mannose-mimicking head-groups", Biomaterials, vol. 33, 2012, pp. 6220-6229.

International Search Report and Written Opinion, completed May 25, 2018, pertaining to PCT/IN2017/050488, filed Oct. 23, 2017.

* cited by examiner

GOLD NANOPARTICLE BASED FORMULATION FOR USE IN CANCER THERAPY

FIELD OF THE INVENTION

The present invention relates to the development of gold nanoparticle based novel formulation by combining gold nanoparticles (AuNPs) with bi-functional recombinant fusion protein [TRAF(C)] to target HER2+ cancers for delivery of biomolecules (anticancer drugs and nucleic acids). These targeted nanomedicine formulations show better therapeutic efficacy both in vitro and in vivo with low toxicity when compared to prior art. The recombinant protein TRAF(C) is a genetically engineered chimeric molecule of TRBP2 domain fused with the affibody which enables the delivery of siRNA to HER2+ cancers in a targeted manner. Using the combinatorial approach, we designed gold nanoparticle-based targeted drug delivery system (TDDS) by combining AuNPs with bi-functional recombinant fusion protein TRAF(C), doxorubicin and siRNA. The nanoparticle-based formulation designated as Au-TR-DX-si was found to be stable and homogenous as revealed by several physicochemical studies. In addition, the fusion protein TRAF(C) has the ability to target HER2+ receptor (heregulin receptors also known as human epidermal growth factor receptor-2) overexpressing ovarian cancer cells (SK-OV-3). The functional activity of the formulation was further evaluated both in vitro and in vivo. Intraperitoneal administration of nanoformulation in SK-OV-3 xenograft nude mice exhibited significant suppression of tumor growth due to co-delivery of ErbB2 siRNA and doxorubicin. In vivo biodistribution confirmed increased accumulation of gold in tumor tissue, which further established the targeting property of the nanoconjugation. We strongly believe that the gold nanoparticle based formulation could be used as a universal strategy for effective treatment of HER2+ cancers.

BACKGROUND OF THE INVENTION

Ovarian cancer is the most common malignancy in women with poor prognosis, which is commonly diagnosed after stage III/IV (Menon, U. et al, The lancet Oncology, 2009, 10, 4; 327-340). For example, in United States alone 21,290 new cases were noticed in women with ovarian cancer and 14,180 death cases were documented (Siegel, R. L. et al, Cancer statistics, 2015, 65; 5-29). There have been significant developments in the treatment of advanced ovarian cancer in recent years but the mortality rate remains high (Konstantinopoulos, P. A. et al, Nature Clinical Practice Oncology, 2008, 5; 10). Several treatment strategies are available for the treatment of cancer including surgery, radiation and chemotherapies. The major disadvantage of the anticancer drugs is poor bioavailability, less specificity, toxic effects in other organs and development of drug resistance during treatment. Therefore, development of targeted drug delivery systems is essential to overcome the problems associated with the chemotherapy (Aatra, C. R. et al, Advanced Drug Delivery Reviews, 2010, 62; 346-361). Malignant tumors proliferate very rapidly by overexpressing the surface growth factor receptors (Hanahan, D. et al, Cell, 2000, 100; 57-70). Heregulin receptors-2 is a tyrosine kinase receptor which activates several genes responsible for the rapid proliferation of cancer cells. During signal transduction, heregulin receptor-2 dimerizes with the other isoforms of the receptor family proteins. Hence the heregulin receptor-2 was considered as the molecular target in the several cancer types. Therefore, in the current invention, we selected the heregulin receptor-2 that specifically overexpress in the ovarian and breast cancer cells.

There are several HER2 binding ligands reported in the literature which selectively targets HER2 receptors (Geng, L. et al, Theranostics, 2015, 5; 10). Alexisa F et al designed the Affibody loaded HER2 targeted delivery system using polymeric nanoparticles as carrier of drug and paclitaxel as chemotherapeutic agent. The results demonstrated that nanoparticle affibody conjugation delivers the chemotherapeutic agents to cancer cells by HER2 receptor specific manner (Alexisa F et al., ChemMedChem, 2008; 1839-1843). However, the study demonstrated only in in vitro system using a different drug (paclitaxel) and didn't show the efficacy in in vivo model. Further, polymeric nanoparticles show entrapment of drug molecules inside it to fabricate the targeted drug delivery systems. This has several limitations mainly release of drug molecules in therapeutic site, as drug or other therapeutic moieties are not attached in the surface of the nanoparticles. Dar et al. also demonstrated that HER-2 binding affibody fused with TRBP2 domain can bind with siRNA in a conformation-specific manner to deliver siRNA in SK-OV-3 ovarian cancer cells (Dar, G. H. et al, Nanomedicine, 2015; 1-12). However the study was conducted by using high dose of targeted ligand and siRNA i.e., 13.6 mg/kg TRAF protein and 2 mg/kg siRNA. These results are promising towards the targeting and treatment of HER2 positive cancer cells using recombinant proteins. However, antitumor efficacy of delivery vehicles was limited because of the high degree of cancer clonal integrity and tumor aggressive nature (Li, F. et al, Int. J. Cancer, 2014, 134; 1257-1269). Hence combination treatment strategies will offer much hope to achieve synergistic effect to eradicate the heterogeneity of cancers by delivering low dosage of the therapeutic agents in a single delivery complex that makes an ideal and efficient vehicle to deliver any therapeutic gene in a stable, non-immunogenic and non-toxic manner. In this regard, researchers were highly engaged with the development of new formulations for the treatment of cancer. The major challenge in the delivery of multiple therapeutic agents is tissue distribution and transport of the delivery vehicles in portal circulation. Nanotechnology plays a vital role for the systemic delivery of drugs and nucleic acids to the malignant cells in a targeted manner. Such strategies synergistically reduce the toxicity of the anticancer drug and increase the therapeutic efficacy. In nanomedicine, gold nanoparticles are widely used in gene and drug delivery because of its unique fundamental properties (chemical, physical, electrical, optical), surface plasmon resonance (SPR), tunable size, ease of synthesis, characterization and surface functionalization. Furthermore, several investigators including our group have demonstrated the utility of gold nanoparticles as delivery vehicles for targeted cancer therapy Gold nanoparticles are the multifunctional platforms for the targeted delivery of therapeutic agents including anticancer drugs and nucleic acids (Peer, D. et al, Nature Nanotechnology, 2007; 2, US 20090148535 A1). Gold nanoparticles are nontoxic, bioinert, and readily synthesized and fabricated (Daniel, M. C. et al, Chem. Rev. 2004, 104; 293-346). These particles can be functionalized to localize specially at tumor sites using different receptor specific ligands for preparation of targeted delivery systems and disease diagnosis applications (Paciotti, G. et al, Drug Dev. Res. 2006, 67; 47-54). Moreover, long history of use of gold nanoparticles in medicine has culminated in several reports that have established its application as a non-toxic platform for disease diagnosis and therapy.

Earlier studies on the polymeric nanoparticles based drug delivery systems, demonstrated the drug delivery to HeLa cancer cells. (WO2015074762). However, the study demonstrated only on the drug delivery and did not discuss about the nucleic acid delivery. Similarly, researchers also used the different fusion proteins in the bio-imaging and labelling of the biomolecules (WO 2012058627 A2). However, this study demonstrated about the labelling of biomolecules but did not show the drug delivery using the fusion proteins. In recent years, delivery of siRNA to the cancer cells is also well developed and researchers designing different approaches to prepare siRNA delivery systems (US20090148535 A1). However, simultaneous delivery of siRNA and drug using the recombinant fusion proteins with nanoparticles system was not reported in earlier studies.

OBJECTS OF THE INVENTION

The ultimate objective of this invention is the development of stable, peptide-loaded HER-2 selective gold nanoparticles-based formulations for the treatment of HER+ cancers to enhance the therapeutic value of these designed therapeutic systems. The prime object of the present invention relates to development of new formulation (Au-TR-DX-si) for the treatment of HER2+ cancers. The second objective of the present invention is to show the effective HER2 receptor targeting and potential tumor suppression activity of nanoformulation in SK-OV-3 xenograft model in nude mice. By conjugating functional protein with gold nanoparticles, as a single complex our nanoparticles-based formulation serves to reduce the dosage of therapeutic agents delivered for the treatment of HER2+ cancers. Anticancer drug and nucleic acids loaded in our nanoparticles formulations work in a synergistic manner and which together activates the apoptosis thereby suppress the tumor growth in vivo.

SUMMARY OF THE INVENTION

Accordingly, the present invention provides gold nanoparticle based new formulation. The nanoformulation contains siRNA and doxorubicin for targeted delivery to HER2+ cancers. The invention discloses the monodispersed and spherical shape of the nanoformulation (Au-TR-DX-si) with an average dimension of ~100 nm. The present invention also reveals the siRNA binding ability of gold nanoparticle bound recombinant protein in nanoformulation. In another embodiment of the present invention, selective targeting and erbB2 gene silencing activities of nanoformulation in HER2+ SK-OV-3 cancer cells was explored. Further, the profound tumor suppression activity of nanoformulation in SK-OV-3 xenograft model was observed. In yet another embodiment of the present invention, the detailed anticancer activity mechanism of nanoformulation was explored. Based on these results together, we strongly believe that the current invention on gold nanoparticle-based new formulation could be used as a universal strategy for effective non-invasive treatment of HER2+ cancers.

In an embodiment of the present invention, there is provided a nanoformulation useful for targeted treatment of cancer cells expressing HER2+ receptors and delivery of anticancer drug to said cancer cells, the nanoformulation comprising:
 a. plurality of gold nanoparticles (AuNP);
 b. a protein;
 c. an anticancer drug; and
 d. Nucleic acid.

Yet another embodiment of the present invention provides the nanoformulation wherein size of the gold nanoparticle is in the range of 10-100 nm.

Still another embodiment of the present invention provides the nanoformulation wherein the protein is a bi-functional engineered recombinant fusion protein TRAF(C).

Another embodiment of the present invention provides the nanoformulation wherein the protein is conjugated to the gold surface (AuNP) using the reactive thiol moiety by introducing a C-terminal cysteine.

An embodiment of the present invention provides the nanoformulation wherein the anticancer drug is selected from the group consisting of doxorubicin, gemcitabine, cisplatin, and methotrexate.

In another embodiment of the present invention, there is provided the nanoformulation wherein the anticancer drug is doxorubicin.

Yet another embodiment of the present invention provides the nanoformulation wherein the dose of doxorubicin is in the range of 0.1. to 2.5 mg/kg.

Still another embodiment of the present invention provides the nanoformulation wherein the nucleic acid is erbB2 siRNA of SEQ ID No.6.

In another embodiment of the present invention, there is provided the nanoformulation wherein dose of siRNA is in the range of 0.1 to 0.25 mg/kg.

In still another embodiment of the present invention, there is provided the nanoformulation wherein the cancer is selected from the group consisting of breast cancer, ovarian cancer, melanoma, glioma, and prostate cancer.

In yet another embodiment of the present invention there is provided a pharmaceutical composition comprising a therapeutic amount of the nanoformulation.

An embodiment of the present invention provides a method of treating cancer cells expressing HER2+ receptors, wherein the method comprises administering to a subject a therapeutically effective amount of the nanoformulation.

Another embodiment of the present invention provides the method of treating cancer cells, wherein the nanoformulation is administered by oral, intravenous, intramuscular, or sub cutaneous route.

In still another embodiment of the present invention, there is provided a process for preparation of the nanoformulation, said process comprising:
 (i) conjugating freshly prepared AuNPs with recombinant fusion protein TRAF(C) to obtain a conjugate;
 (ii) incubating the conjugate obtained in step (i) for 30 min at room temperature and constantly stirring to form Au-TR complex;
 (iii) conjugating doxorubicin (DX) to the Au-TR complex obtained in step (ii) and incubating for 30 mins at room temperature to obtain an intermediate conjugate;
 (iv) centrifuging the intermediate conjugate obtained in step (iii) at 15,000 rpm for 45 min at 19-21° C. to form Au-TR-DX complex;
 (v) incubating the Au-TR-DX complex obtained in step (iv) with 5:1 mole ratio of siRNA for 30 minutes to obtain the nanoformulation.

In yet another embodiment the invention provides a process for the preparation of nanoformulation, comprising the steps:
 i) providing freshly prepared AuNPs and recombinant fusion protein TRAF(C);

ii) conjugating nearly 50 mL of AuNPs with nearly 100 μg of TRAF(C) as provided in step (i);
iii) incubating the conjugate obtained in step (ii) for nearly 30 min at room temperature and constantly stiffing to form Au-TR complex;
iv) conjugating nearly 125 μg of doxorubicin (DX) to the Au-TR complex obtained in step (iii) and incubating it for nearly 30 mins at room temp;
v) centrifuging the conjugate obtained in step (iv) at nearly 15,000 rpm for nearly 45 min at 19-21° C. to form Au-TR-DX complex;
vi) incubating Au-TR-DX complex obtained in step (v) with 5:1 mole ratio of siRNA for nearly 30 minutes to form Au-TR-DX-si complex;

In yet another embodiment the invention provides use of the nanoformulation as an anti-metastatic agent.

In yet another embodiment the invention provides use of the nanoformulation in treating drug-resistant tumors.

In yet another embodiment the invention provides use of the nanoformulation in the treatment of genetic disorders.

In yet another embodiment the invention provides use of the nanoformulation for imaging upon non-invasive delivery, when partly labeled with fluorophores.

BRIEF DESCRIPTION OF ACCOMPANYING DRAWINGS

FIG. 1 illustrates schematic fabrication of gold nanoparticle based formulation Au-TR-DX-si conjugated with purified TRAF(C) fusion protein for the delivery of doxorubicin and siRNA to HER2+ ovarian cancer in vitro and in vivo: Purified recombinant fusion protein TRAF(C) was conjugated to gold nanoparticles and the complex Au-TR was further complexed with an anti-cancer drug doxorubicin and siRNA.

Figure 2:
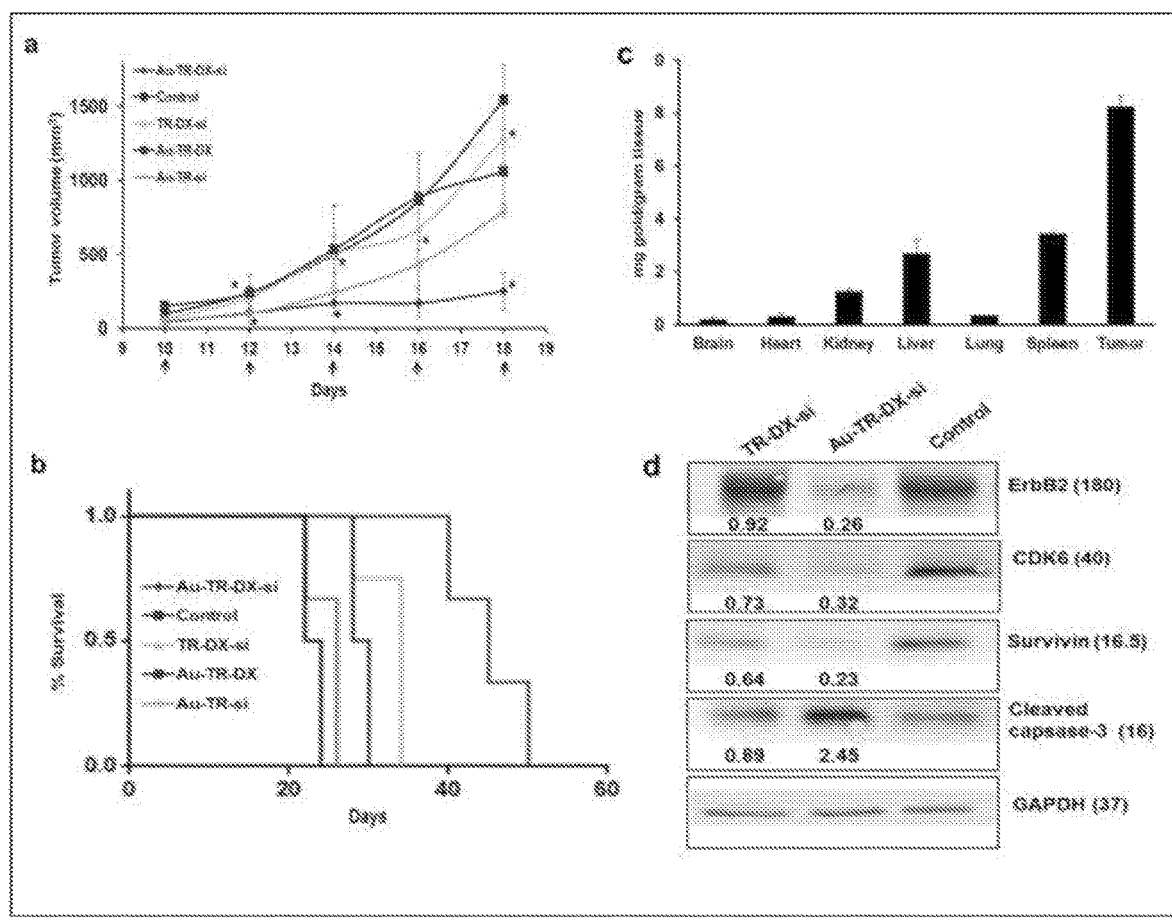

FIG. 2 depicts in vivo studies: a) Tumor regression studies in SK-OV-3 xenograft nude mice. A therapeutic dose to co-deliver erbB2 siRNA and doxorubicin was optimized by preparing complexes containing 2.5 mg/kg doxorubicin and 0.25 mg/kg siRNA. Formulations were administered via intraperitoneal route (IP). The graph depicts suppression of tumor growth in Au-TR-DX-si treated groups compared to controls which indicates synergistic effects and specificity of the formulation Au-TR-DX-si. b) Survival curve shows percent survival of Au-TR-DX-si-treated group vs controls. c) Biodistribution of Au-TR-DX-si by ICP-OES analysis. The results show the higher accumulation of gold in tumor tissues compared to other body organs d) Western blot analysis of erbB2 levels in SK-OV-3 tumors from TR-DX-si and Au-TR-DX-si treated groups. The blot depicts erbB2 knockdown in the Au-TR-DX-si complex treated tumor tissue compared to controls. The levels of survivin, cyclin-dependent kinase (CDK6) were downregulated and upregulation of cleaved caspase-3 (Asp175) was observed in mice treated with Au-TR-DX-si Western blot analysis of SK-OV-3 tumor lysates from Au-TR-DX-si-treated and control group (define control). The values below treated groups indicates the relative density compared to control (=1). All the values were obtained using ImageJ normalized to respective GAPDH (internal control). The numerical within brackets indicate the molecular weight of the respective proteins in kDa.

Figure 3:
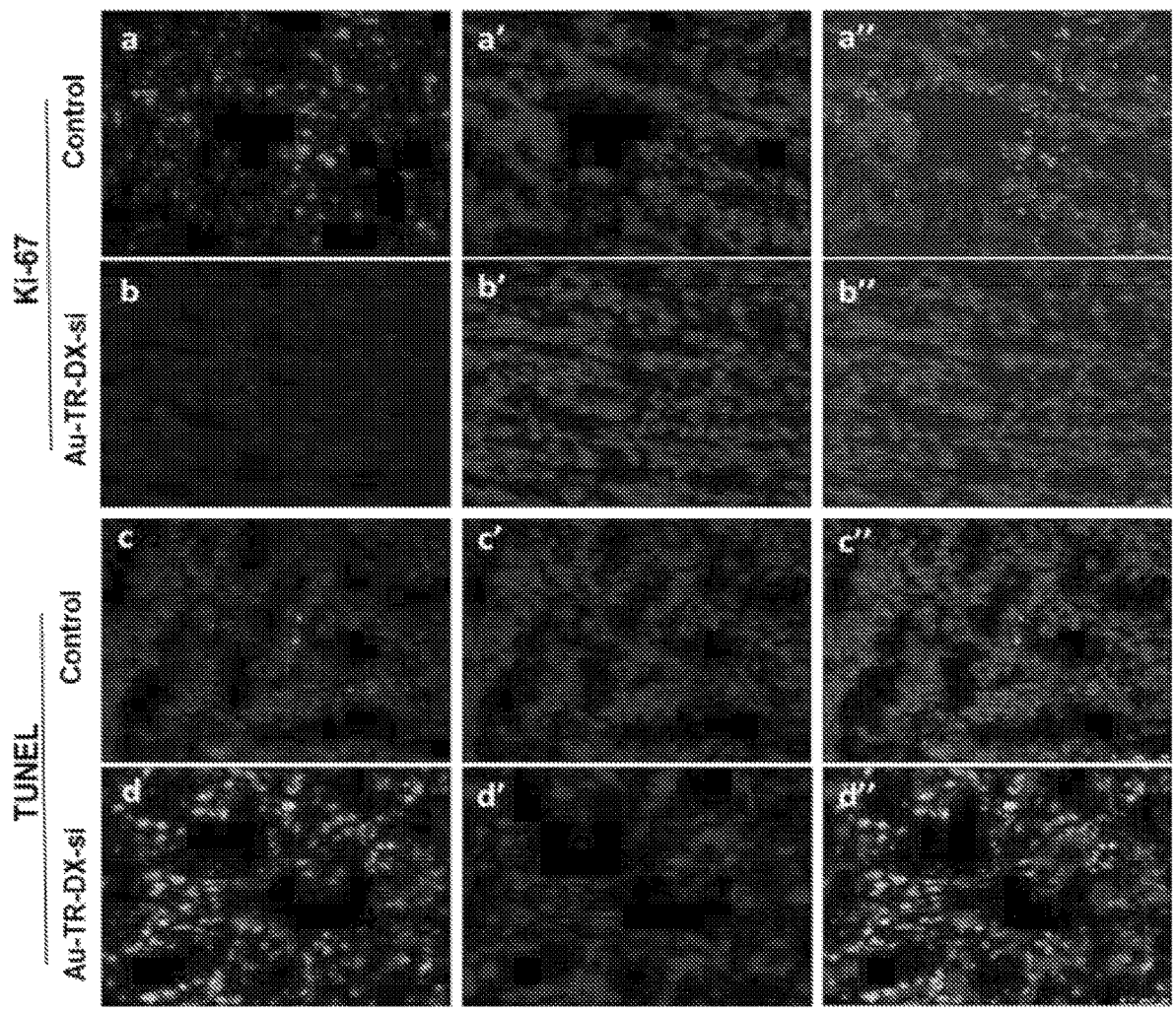

FIG. 3 shows immunohistochemistry of tumor tissues (Top two rows) Ki-67 expression in tumor tissues: Representative images depict the downregulation of Ki67 expression in Au-TR-DX-si-treated tumors compared to control. Red fluorescence in 'a' and 'b' originate from DyLight633. Nuclei are stained with DAPI (blue). 'a' and 'b' are the merged images of the respective panels. (Bottom two rows): TUNEL assay: DNA damage in the SK-OV-3 tumor tissues depicts apoptosis in Au-TR-DX-si-treated tumors compared to control. 'c' and 'd'-green fluorescence from FITC, 'c' and 'd'—blue fluorescence from DAPI. Merged fluorescence images are depicted in 'c' and 'd'.

Figure 4:
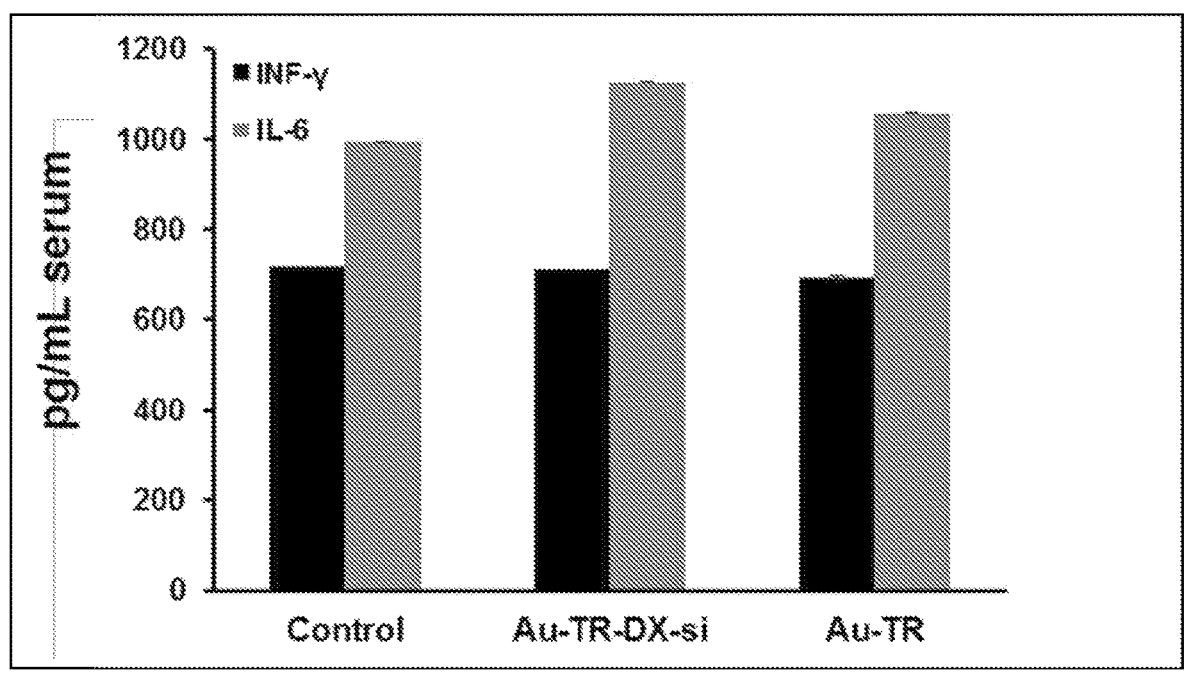

FIG. 4 shows analysis of serum cytokine levels of treated mice by ELISA. C57/BL/6 mice were treated with Au-TR and Au-TR-DX-si and compared to untreated groups. Graph depicts measurement of IFN-γ and IL-6 levels in serum after intraperitoneal injection. No significant change in IFN-γ and IL-6 levels confirm the not toxic nature of the complex.

DETAILED DESCRIPTION OF THE INVENTION

In the present innovation, we designed the new formulations which utilize the minimum dose for simultaneous delivery of doxorubicin and erbB2 siRNA with TRAF(C) loaded gold nanoparticles. In light of the aforesaid reports, our system is more advanced and show higher therapeutic efficacy due to the co-delivery of therapeutic agents for treating ovarian cancer.

TRAF(C) protein loaded gold nanoparticles system is new formulation which is not discussed in any other earlier studies including from our group. In the present innovation, we mainly focused on the development of a new advanced drug delivery system with our gold nanoparticles. Due to their excellent tissue penetration properties and distribution, low dose of therapeutic agents will give the higher therapeutic efficacy. Moreover, the targeted ligand TRAF(C) used in our nanoformulation is a variant of TRAF developed in our group and not published in any other studies. With all these examples we believe that our new formulation could be considered as new generation of nanomedicne for the treatment of ovarian cancer. With the evidence of developing superior carriers for nucleic acids (siRNA/plasmid DNA) therapeutics by improving the overall physiological stability, we earlier demonstrated that bio-inspired fusion proteins (TRAF) can target human epidermal growth factor receptor-2 (also known as heregulin receptor-2:HER2) (Dar G. H. et al, Nanomedicine, 2015; 1-12; Govindarajan, S. et al, Biomaterials, 2012; 33; 2570e2582).

In the present invention, the potential of engineered fusion protein (TR) for targeted cancer therapy was further explored by the generation of protein-conjugated gold nanocarriers to target HER2+ ovarian cancer. With the combined attributes originating from these sources, we fabricated and designed gold nanoparticles (AuNPs/Au) to generate a targeted drug delivery system (TDDS) where a recombinant bi-functional fusion protein (TR), was conjugated to the gold surface using the reactive thiol moiety by introducing a C-terminal cysteine to generate a new and novel variant of TRAF (Dar G. H. et al, Nanomedicine, 2015; 1-12) denoted as TRAF(C) also termed as TR. The gold nanoparticle-based nanoformulation (Au-TR-DX-si) was designed by combining AuNPs with bi-functional recombinant fusion protein TRAF(C)/TR, doxorubicin (DX) and siRNA. The nanoformulation outlined in Scheme 1 was characterized in detail and subsequently evaluated for its targeting potential in vitro and in vivo.

The present innovation relates to the development of gold nanoparticle-based new formulations for the targeted delivery of nucleic acids and anticancer drugs to HER2+ cancer cells. The novelty of the present innovation is the targeted delivery of the therapeutic agents (nucleic acids and anticancer drugs) using recombinant proteins loaded gold nanoparticle as two novel formulations. However, prior studies also show the utilization of affibody and other targeting ligands for the delivery of therapeutic agents using different nanoparticles. But the co-delivery of erbB2 siRNA and doxorubicin in HER2 cancer therapy was not studied earlier with gold nanoparticle system using recombinant proteins together in one system. The advantage of the present innovation is that the formulations permits the usage of low dose of therapeutic agents (2.5 mg/kg of doxorubicin and 0.25 mg/kg erbB2 siRNA) in ovarian tumour xenograft mice model which showed the synergistic effects of doxorubicin and siRNA with 6 fold tumour regression in vivo upon systemic delivery. The recombinant protein TRAF(C) used in our formulation is a variant of TRAF protein with a C-terminal cysteine that was engineered in the recombinant construct. This variant has not been reported earlier and we used the newly designed recombinant protein chimera for the conjugation with gold nanoparticles for the first time to prepare targeted drug delivery system. Altogether, the gold nanoparticle-based formulation is a new generation nanomedicine which is stable upon in vivo delivery and enables decreasing the dose of the therapeutic agents and enhances the activity in ovarian cancer upon non-invasive delivery. Overall, the present formulation shows low usage of therapeutic molecules, better therapeutic efficacy, less toxicity.

EXAMPLES

The following examples are given by way of illustration of the present invention and therefore should not be construed to limit the scope of the present invention Example-1-A Procurement Details Sodium borohydride (NaBH$_4$), chloroauric acid (HAuCl$_4$), Dulbecco's modified Eagle's medium (DMEM), trypsin from bovine pancreas, RIPA buffer, protease inhibitor cocktail (PIC), TRIzol reagent, Hoechst, fluoroshield with DAPI mounting medium and BCIP-NBT (Premixed) solution were purchased from Sigma (St. Louis, Mo., USA). Doxorubicin was purchased from Alfa Aesar. Primers were synthesized by Bioserve Technologies, Hyderabad. Human GAPDH siRNA was purchased from Ambion (Life Technologies) for the characterization studies. For gene silencing experiments, validated Human ErbB2 siRNA was purchased from Dharmacon (GE Heathcare). Carboxyfluoroscein (FAM)-labelled siRNA were purchased from Eurogentec. Commercially available cell lines SK-OV-3 (ATCC Cat # HTB-77) and MDA-MB-231 (ATCC Cat # HTB-26), A549 (Cat # CCL-185), PANC-1 (ATCC Cat # CRL-1469) cell lines were purchased from ATCC. B16F10 cell line was purchased from NCCS, Pune, India. The cytoplasmic domain of ErbB2 antibody was purchased from Millipore (Cat #05-1047). GAPDH antibody (5174P), Ki67 antibody (Cat # PA5-19462), Dylight-633 conjugated secondary antibody (Cat #35563) were purchased from Thermo Scientific. Cleaved Caspase-3 (Asp175) (5A1E) Rabbit mAb (Cat #9664P) was purchased from cell signaling technology.

Example-1-B

Construction, Sub Cloning of the Expression Cassette and Expression of the Gene Encoding Chimeric Fusion Protein TRAF(C)

Briefly, recombinant fusion protein TR, gene sequence from mammalian cell lines (Dar G. H. et al, Nanomedicine, 2015; 1-12) corresponding to the second domain (TARBP2/TRBP2, Sequence ID: NCBI Reference Sequence: NM_134323.1) together with a pentaglycine linker, the affibody sequence and a C-terminal cysteine codon was amplified by overlap PCR. The final amplicon was cloned in pET28a plasmid to generate N-terminal His-tagged fusion constructs to facilitate protein purification. Selected recombinants were expressed in *E. coli* BL21 (DE3) and purified to homogeneity using Ni-NTA affinity matrix. *E. coli* BL21 (DE3) cells overexpressing the recombinant proteins were lysed under denaturing conditions using lysis buffer (50 mM sodium phosphate buffer pH=7.4 consisting 300 mM NaCl, 10 mM Tris, 6 M urea and 1 mM PMSF), sonicated and centrifuged at 18,000 rpm for 20 min to pellet cell debris. The supernatant was then incubated with the pre-equilibrated Ni-NTA sepharose resin for 1 h and then loaded onto a column and washed with 0.1% Triton X-114 in lysis buffer at 4° C. This step is required to remove the bacterial endotoxins. The bound protein was refolded under native conditions and eluted using sodium phosphate buffer (pH=7.4) containing 300 mM imidazole by on-column refolding. The eluted fractions were pooled, desalted by Sephadex G25 column and buffer exchanged in phosphate buffered saline (PBS: pH=7.4). The fusion protein was validated by MALDI-TOF, SDS-PAGE and evaluated for its ability to bind siRNA. The molecular weight of TRAF(C) was confirmed by the SDS-PAGE analysis using standard molecular mass marker. The MALDI-TOF results further indicated that the purified TRAF(C) molecular weight at 18.6 k·Da. The gel binding assay of purified TRAF(C) with siRNA at reveals that 5:1 and 10:1 ratios were completely bound with siRNA.

Example-2

Preparation of AuNPs for the Conjugation of TR Fusion Protein to AuNPs (Au-TR)

AuNPs were freshly prepared for all the biological experiments. Initially AuNPs were prepared by using the sodium borohydride reduction method as previously described (Patra, C. R. et al, Advanced Drug Delivery Reviews, 2010, 62; 346-361). Briefly $10^{-2}$(M) tetrachloroauric acid (HAuCl$_4$) solution was added to 100 mL using sterile Millipore water (18.2 mΩ) and 50 mL of 0.05 mg/mL of sodium borohydride solution was added under constant stirring overnight. Recombinant fusion protein TR was conjugated to AuNPs based on established procedures (Patra, C. R. et al, Advanced Drug Delivery Reviews, 62; 346-361). Briefly, AuNPs were incubated with the TR fusion protein (0.7 mg/mL) at different concentrations for 30 min under constant stirring. A series of tubes each with 1 mL of AuNPs were taken and incubated with increased concentrations of TR. After incubation, the absorbance of all conjugated and unconjugated AuNPs were recorded in the UV-visible spectrophotometer (JASCO dual-beam spectrophotometer; Model V-650). The observed change in the absorbance was recorded for all formulations in a spectrophotometer with respect to free gold nanoparticles. A saturation curve of TR-bound AuNPs was generated by plotting the absorbance values as a function of concentration of TR used for the conjugation. The resultant formulation is denoted as Au-TR for clarity. The characteristic surface plasmon resonance band at ~512 nm, obtained by UV visible spectroscopy indicates the formation of spherical gold nanoparticles, which is further confirmed by TEM. There is an increase of absorbance of AuNPs after addition of increasing concentration of TR up to 4 µg/mL, suggesting the perturbation of the electrical double layer around gold nanoparticles upon TR addition.

Example-3

Attachment of DX to Au-TR (Au-TR-DX)

Anticancer drug DX was conjugated to Au-TR prepared in the earlier section. Saturation curve was generated by adding different concentrations of DX to the Au-TR under constant stirring. After 30 min, all the formulations were analyzed by UV-vis spectroscopy (JASCO dual-beam spectrophotometer; Model V-650). The attachment of DX to the surface of AuNPs was achieved in a layer-by-layer fashion using a two-step incubation process. Au-TR-DX nanoconjugate was prepared by incubation of AuNPs with half saturation concentration of TR (2 µg/mL) followed by different concentration of DX (1-5 µg/mL). A further increase in the absorbance of AuNPs after addition of DX to Au-TR solution indicated the perturbation of the electrical double layer present around AuNPs suggesting the further attachment of DX with Au-TR in Au-TR-DX. The SPR spectra of Au-TR-DX showed an increased absorbance at 2.5 µg doxorubicin/mL Au-TR. Beyond this concentration, intensity of absorbance decreases indicating slight aggregation of the nanoconjugates. We examined the stability of naked AuNPs and gold nanoconjugate (Au-TR & Au-TR-DX) in 10% NaCl solution. According to absorbance data, naked AuNPs (without conjugation) aggregated upon the addition of 10% NaCl. In contrast, under identical salt conditions, TR-loaded gold nanoparticles (Au-TR) and DX loaded Au-TR remained stable.

Example-4

Preparation of Nanoformulation

The following formulations were prepared on a large scale by incubating 50 mL of AuNPs with 100 µg of TR for 30 min following which 125 µg of doxorubicin was added and incubated for another 30 min. This was then centrifuged at 15,000 rpm for 45 min at 20° C. (Thermo-scientific (WX-Ultra series) and a dark red pellet was obtained, which was used for all the in vitro and in vivo experiments.
1. Gold nanoparticles: AuNP
2. Au-TRAF(C): Au-TR
3. Au-TR-Doxorubicin: Au-TR-DX
4. Au-TR-DX-siRNA: Au-TR-DX-si Example-5

Association of siRNA with Au-TR Complex

In order to determine the siRNA binding ability of Au-TR complex, we performed the binding assays by preparing the complex using GAPDH siRNA. Following incubation with Au-TR for 30 min, the complex was electrophoresed on a 15% native PAGE using TBE (1× tris-borate-EDTA) running buffer in Biorad vertical electrophoresis system. The complex preparation ideally included 10 pmole of siRNA that was incubated with the Au-TR complex by taking the different mole ratios of gold nanoparticle bound peptide and siRNA (1:1, 5:1 and 10:1). Free siRNA (10 pmole) was used as positive control. Following electrophoretic separation, the gel was stained with ethidium bromide and visualized using the UV gel docking system (UVItec Gel doc). The gel binding pattern of siRNA to Au-TR indicates the efficient binding at 5:1 and 10:1 mole ratio (Au-TR:si). However, based on the binding results, we considered the 5:1 mole ratio of siRNA to Au-TR for optimized Au-TR-si nanocomplex, which was used for further in vitro and in vivo experiments.

Example-6

Transmission Electron Microscopy

The size and shape of the nanoformulation was analyzed by using the TEM method. After centrifugation of Au-TR-DX conjugates at 15,000 rpm for 45 minutes at 20° C. (Thermo-scientific (WX-Ultra sense), the loose pellet was dissolved in Millipore water and submitted for TEM analysis (200 KV Transmission Electron Microscope from JEOL, Japan). The formulations examined in this invention indicated the consequential increase in the size of the nanoparticles upon the conjugation of TR, DX, and si.

Example-7

XRD Analysis of Gold Nanoformulations

XRD pattern of AuNPs, Au-TR and Au-TR-DX complexes were performed to analyze the surface structure pattern of gold nanoparticles. After conjugating the biomolecules on the surface of the gold nanoparticles, the AuNPs, Au-TR and Au-TR-DX complexes were coated on a glass slide and submitted for XRD analysis. (Bruker D8 Advance Powder X-ray diffractometer). The XRD patterns of the Au-TR-DX and Au-TR was found to be similar to free AuNPs. The results demonstrate that the crystallinity of AuNPs was not affected upon addition of proteins and drug molecules.

Example-8

Dynamic Light Scattering (DLS) Measurements

The hydrodynamic radius and zeta potential of the nanoformulation was measured by using the DLS technique. Initially the nanoformulation was prepared as mentioned in the above section and diluted with the Millipore water to analyze the size and charge using DLS instrument. Similarly, the size and charge of the AuNPs, Au-TR and Au-TR-DX, Au-TR-DX-si was also determined. The size of AuNPs alone was found to be 5.3 nm with a negative zeta potential −60 mV, which increases upon conjugation with TR to ~30 nm with a negative zeta potential of −38.9 mV. Further significant increase in the dimension and zeta potential was observed upon the addition of DX (65 nm/−30.3 mV) reaching a maximum upon the addition of siRNA (si) (105 nm/−48 mV).

Example-9

FT-IR Analysis of Gold Nanoformulations

In order to analyze the functional groups present in the Au-TR and Au-TR-DX complexes, FT-IR analysis was performed. The nanocomplexes were processed as described in above example and submitted for FT-IR analysis (Thermo Nicolet Nexus 670 spectrometer). The attachment of DX to the surface of Au-TR was further confirmed by Fourier transform infrared spectroscopy (FTIR). The free doxorubicin shows the peak at 1524 cm$^{-1}$ which is shifted to 1542 cm$^{-1}$ indicating the possible weak covalent bonding between Au—NH$_2$. Further, the another peak in Au-TR at 3422 cm$^{-1}$ shifted to lower frequency (3417 cm$^{-1}$) for Au-TR-DX indicating possible dative bonding (Au—OH) between —OH group of doxorubicin with gold nanosurface. Moreover, zeta potential of Au-TR-DX (−30.3 mV) significantly decreased from that of Au-TR (−38.9 mV). This result indicates the possible electrostatic interaction between negatively charged Au-TR with positively charged naked doxorubicin. Altogether, the FTIR and zeta potential studies indicate the nature of bonding between Au-TR and doxorubicin may be electrostatic as well as dative bonding.

Example-10

Doxorubicin Release Analysis from Nanoformulation

In order to analyze the kinetics of doxorubicin release from nanoformulation, spectroscopic method was employed. The pellet of nanoformulation was prepared as previously described and suspended in pH=6 and pH=7.4 PBS buffers and incubated in room temperature. The solutions were centrifuged periodically at different time intervals. The supernatant of the solution was measured for the doxorubicin absorbance. The results indicate that slow and sustained release of doxorubicin in both pH=7.4 and 6 buffers.

Example-11

HER2 Receptor Expression Analysis

HER2 expression levels in different cancer cells were analyzed by western blotting using Anti-ErbB 2 antibody. Different cancer cells were chosen to analyze the HER2 receptor expression. Initially, SK-OV-3, MDA-MB-231, A549, PANC-1 and B16F10 cells were grown in 60 mm dishes and lysed with RIPA (Radio immune precipitation assay) buffer containing PIC 1(×) (Protease inhibitor cocktail). Protein concentration was estimated by using the Bradford method (Bradford, M. M. et al, *Anal Biochem.* 1976, 72: 248-54). The protein samples were electrophoresed in 6% polyacrylamide gel (Laemmli, U. K. et al, *Nature,* 1970, 227: 680-5) and blotted to on the PVDF membrane. Nonspecific sites were blocked with 5% nonfat milk for 2 hours in room temperature and incubated with anti HER2 antibody overnight at 4° C. Unbound antibodies were removed by washing with TBST solution. Goat anti-rabbit alkaline phosphatase conjugated secondary antibody was used to detect the primary antibodies and developed with BCIP-NBT (5-bromo, 4-chloro indolyl phosphate-Nitro blue tetrazolium) reagent. The results indicate the high levels of HER2 in SK-OV-3 which may contribute to severe malignancy. The analysis of HER2 receptor expression enabled us to choose these cells for ensuing targeting studies Example-12

HER2+ Receptor Mediated Uptake of Nanoformulation

Receptor-specific cellular uptake of nanoformulation was performed by laser scanning confocal microscopy using the cell-line pair i.e. HER2 overexpressing SK-OV-3 cells considered as HER2 positive (HER2+) and low expressing HER2 MDA-MB-231 cells as HER2− receptors considered as negative. Cells were plated on sterile cover slips and treated with nanoformulation complexes for 90 min in serum-free DMEM media. Similarly cells were treated with free doxorubicin, unconjugated AuNPs and Au-TR as positive controls. After the incubation period, cells were washed thoroughly with PBS and fixed in 4% formaldehyde for 5 min followed by washing with PBS twice. Cellular nuclei were counterstained with Hoechst-33258 and mounted in Vectashield mounting medium H-100 (Vector Laboratories, Inc.). The fluorescence from the Cy5-labeled siRNA (Ex$\lambda$ 650/Em$\lambda$ 670) and fluorescence from the doxorubicin (Ex$\lambda$ 460/Em$\lambda$ 570), Hoechst-33258 (Ex$\lambda$ 352/Em$\lambda$ 461) was collected using 60× objective lens on Leica LAS-AFTCS-SP5. The images were analyzed by LAS AF software provided by the company. Specific uptake of nanoformulation evident in SK-OV-3 cells was confirmed by the visualization of intense fluorescence ($^{Cy5}$siRNA) and intrinsic fluorescence originating from doxorubicin. In comparison, lack of fluorescence in MDA-MB-231 when compared to SK-OV-3 cells suggests targeting potential and receptor density may have contributed to high accumulation of the nanoformulation that has contributed to increase in uptake in SK-OV-3.

Example-13

Analysis of Nanoformulation Uptake by Flow Cytometry

The amount of DX internalized following uptake of nanoformulation complex was analyzed in SK-OV-3 by FACS. SK-OV-3 were cultured in 60 mm dishes and treated with nanoformulation complex and free doxorubicin for 3 h. Following incubation, cells were washed thoroughly with DPBS and trypsinized. The cell suspension was then analyzed by FACS (FACScan flow cytometer (BD Bioscience) to assess the amount of doxorubicin internalized from the Au-TR-DX-si treated with SK-OV-3. Shift in the fluorescence peak confirms the uptake of nanoformulation where 70% of cells were positive.

Example-14

Cellular Uptake Analysis of Au By ICP-OES

To quantitate the gold content as a measure of the extent of uptake, we evaluated cellular uptake of nanoformulation complex by ICP-OES as previously described. HER2 positive SK-OV-3 and HER2− MDA-MB-231 cells were seeded in 100 mm dishes to 70% confluence. The following day, cells were treated with nanoformulation and incubated for 2 hours followed by thorough PBS washes. The cells were trypsinized and counted using hemocytometer and centrifuged. Both SK-OV-3 and MDA-MB-231 cells pellets were digested with 85% nitric acid for 48 h at 50° C. followed by analysis by ICP-OES to analyze the gold content. ICP-OES analysis of cells treated with nanoformulation indicated high gold content in treated SK-OV-3 cells, which further confirms receptor-specific internalization of nanoformulation Example-15

Reverse Transcription and Polymerase Chain Reaction

The mRNA expression levels of erbB2 in tumor samples were analyzed by reverse transcriptase PCR (RT-PCR).

Total RNA was isolated from the tumor tissues using the TRIzol reagent. The isolated RNA was subjected to one step RT-PCR using 50 ng of RNA with master Amp™ high fidelity RT-PCR kit (Epicentre Biotechnologies # RF1025). Beta actin and erbB2 sequences were amplified using the respective gene specific primers. The primer sequences (5'-3') are: Human beta actin forward GCCAACCGCGA-GAAGATG Human beta actin reverse CATCACGATGC-CAGTGGTA, erbB2 Forward TGTGAACCTGACCTCT, erbB2 Reverse TTGTCATCCAGGTCCACACAGGAGT. The results showed that nanoformulation has resulted in significant knockdown of erbB2 gene. The results were quantified by ImageJ analysis.

Example-16

In Vivo Studies: Delivery of Au-TR Complex in Xenograft Nude Mouse Model

All experiments with nude mice were conducted in accordance with protocols approved by the Institute's Animal Ethics Committee (IAEC) vide approval #81/2014 and #69/2015). Nude mice were injected subcutaneously with SK-OV-3 cells ($5\times10^6$ per mouse) in right flank region. The tumors were measured with Vernier calipers and allowed to grow till the tumors attained a size of ~50-100 mm$^3$. The mice were divided into five groups namely i) Untreated control ii) (Au-TR-DX-si) (2.5 mg/kg doxorubicin, 0.25 mg/kg siRNA) iii) TR-DX-si (2.5 mg/kg doxorubicin, 0.25 mg/kg siRNA) iv) Au-TR-DX (2.5 mg/kg doxorubicin) and v) Au-TR-si (0.25 mg/kg siRNA).

Example-17

Delivery of siRNA and Doxorubicin

Treatment was initiated upon the attainment of tumor volumes in the range 40-60 mm$^3$ by injecting the formulations via the intraperitoneal route (IP). We non-invasively co-delivered erbB2 siRNA and DX to evaluate in vivo anti-cancer activity. The treatment regimen consisted of 5 injections injected every alternative day. The tumors were measured using the formula ($0.5\times ab^2$) where 'a' represents the longest dimension and 'b' represents the shortest dimension. To show our hypothesis that co-delivery of erbB2 siRNA doxorubicin give the synergistic effects for tumor regression, we designed different treatment groups containing SK-OV-3 xenograft. The treatment groups are mice treated with Au-TR-si, Au-TR-DX, Au-TR-DX-si and TR-DX-si. From the tumor regression curve it is evident that mice group treated with Au-TR-DX-si showed the significant tumor regression compared to other mice groups treated with individual therapeutic agents. However, Au-TR-DX and Au-TR-si treated groups also exhibited the tumor regression but co-delivery of erbB2 siRNA and doxorubicin in one single formulation showed more tumor suppression than the above two groups. A 6-fold difference in tumor volume indicates maximal efficacy of nanoformulation compared to untreated control. The tumor regression pattern is the proof of our hypothesis that Au-TR-DX-si gives the synergistic effects. Interestingly, in another experiment condition we delivered erbB2 siRNA and doxorubicin without gold nanoparticle conjugation. The tumor regression was not observed in this group. This indicates that nanoformulation of TRAF (C), erbB2 siRNA and doxorubicin effectively showed the potent anticancer activity in mice. Additionally, we observed the survival rate of the nanoformulation administered group in comparison with control. The results indicated that the life span of nanoformulation treated mice was enhanced compared to control group.

Example-18

Biodistribution

Nude mice carrying SK-OV-3 xenograft were injected with nanoformulation through intraperitoneal rout and sacrificed 24 h post-delivery. The essential organs like heart, kidney, liver, brain, lungs and tumor were collected in ice cold PBS and stored in −80° C. Tumor tissues from each mouse were digested in 80% nitric acid and incubated in a water bath for 50° C. After 48 h, the digested tissue samples were filtered and submitted for analysis by ICP-OES to determine the gold biodistribution. ICP-OES analysis reveals that administration of nanoformulation in tumor-bearing mice led to specific and significant localization of AuNPs in tumors tissues when compared to other organs.

Example-19

In Vivo erbB2 Gene Silencing

The tumor tissues from mice treated with nanoformulation and other control groups were collected in ice-cold PBS. The tumor lysate was prepared by homogenization in RIPA buffer containing 1(x) PIC (Protease inhibitor cocktail). The lysate was then centrifuged at 12000 rpm for 30 min and protein amounts of the supernatant of all tumor lysates were estimated prior to electrophoresis on 8% denaturing PAGE. ErbB2 gene knockdown was analyzed by western blotting with anti-erbB2 antibodies to determine the expression levels and quantified by using ImageJ software. Similarly we also probed the membrane with anti-survivin, anti-CDK6 and anti-caspae-3 antibodies. We observed that efficient delivery of erbB2 siRNA by nanoformulation has led to gene silencing of endogenous erbB2 m-RNA levels when compared to TR-DX-si and untreated groups. Further, the levels of survivin and cyclin-dependent kinase (CDK6) were downregulated in the nanoformulation treated group. Survivin is well known as anti-apoptotic protein in cancer cells. As seen from the blot, down regulation of this protein may have led to apoptosis in tumor treated with nanoformulation. Cyclin dependent kinase 6 (CDK6) is a cell cycle regulator with a role in cancer cell proliferation, was earlier observed to interact with doxorubicin as a part of its anticancer mechanism In contrast, analysis of CDK6 expression levels in nanoformulation treated lysate indicated down regulation in nanoformulation treated group. We next analyzed the upregulation of cleaved caspase-3 (Asp175) in the treated nanoformulation group, which brings to light the activation of apoptosis pathway in the mice group administered with nanoformulation which contributes to effective tumor suppression.

Example-20

Immunohistochemistry of SK-OV-3 Tumor Tissues

The proliferation marker (Ki-67) in the tumor tissues of nanoformulation treated and untreated animals were performed by immunohistochemistry. Briefly, the tumor sections were fixed in isopropanol and washed twice with PBS. Antigen retrieval was performed by using citrate buffer at 65° C. for 10 min. The sections were then incubated with respective Ki-67 antibodies overnight at 4° C. All the sections were thoroughly washed with TBST thrice and incubated with Dylight-633-conjugated secondary antibody for 30 min at room temperature. The slides were mounted in fluoroshield with DAPI mounting medium and observed in confocal microscopy. For Dylight633 red fluorescence was acquired at excitation Ex$\lambda$ 638 emission E$_m\lambda$658 nm and for DAPI blue fluorescence was acquired by exiting at Ex$\lambda$ 358 nm and emission at Ex$\lambda$ 461 nm. The confocal images of untreated SK-OV-3 tumor sections showed the intense bright red fluorescence in the nucleus indicating the higher levels of Ki-67 expression. In contrast, in nanoformulation treated mice, the down regulation of Ki-67 expression, evidenced by decreased red fluorescence in the cell nucleus, and indicated lack of proliferation.

Example-21

Terminal Deoxynucleotidyl Transferase (TdT) dUTP Nick-End Labeling (TUNEL) Assay DNA damage is a main event that is indicative of the apoptosis. This was determined through the TUNEL assay carried out to analyze the activation of apoptosis in the SK-OV-3 tumor tissues after treatment with nanoformulation. Initially, tumor sections were fixed in isopropanol and processed using the BD Science TUNEL assay kit. The dehydrated sections were washed twice with PBS and treated with 20 µg/mL of protease K solution for 15 min. The slides were washed twice with wash buffer and incubated for 60 min in 50 µL of DNA labeling solution containing TdT enzyme and FITC dUTPs. The sections were further washed with washing buffer for 2 times and mounted in fluoroshield DAPI mounting medium and observed under confocal microscopy. The results indicated that control tumor sections did not exhibit any green fluorescence compared to nanoformulation which showed the bright green fluorescence in the nucleus indicating activation of apoptosis.

Example-22

Serum Cytokine Production Assay

The serum levels of IL-6 and IFN-$\gamma$ were determined by ELISA (Enzyme linked immunosorbent assay) method as previously described (Srinivas, R. et al, Biomaterials, 2012, 33; 6220e6229). C57/BL6 male mice were divided into three groups (n=3) namely 1) Untreated 2) mice treated with nanoformulation 3) Au-TR treated mice. The blood serum was collected after 20 h of injection and the levels of IL-6 and IFN-$\gamma$ was determined by Quantikine ELISA kit (R&D MIF00). The serum samples were incubated with the pre-coated wells and allowed to interact for 2 h at room temperature. The wells were aspirated and washed with wash buffer four times. The wells were again incubated with mouse IL-6 and IFN-$\gamma$ conjugates in the respective ELISA plates. After the incubation period, 100 µL of substrate solution was added to each well followed by 100 µL of stop solution. The absorbance was then recorded at 450 nm and the levels of IL-6 and IFN-$\gamma$ were expressed in picogram/mL by extrapolation from the respective IL-6 and IFN-$\gamma$ standard curves. The ELISA results showed that the serum levels of IFN-$\gamma$ significantly remain unchanged after treatment with nanoformulation and Au-TR complex compared to untreated groups. Similarly, no significant change in IL-6 levels was observed in the both Au-TR-DX-si and Au-TR complex groups compared to untreated control mice indicating the non-immunogenic nature of nanoformulation.

ADVANTAGES OF THE PRESENT INVENTION

The gold nanoparticles-based new nanoformulation which is stable and selectively targets the HER2 receptors in ovarian cancer cells upon systemic delivery through non-invasive procedures. The formulations carry the engineered recombinant protein (TRAF(C) comprising the two functional domains for nucleic acid binding as well as HER2 receptor binding. Hence the recombinant protein loaded nanoparticles could be useful for the targeted delivery of nucleic acid and anticancer drugs. Due to the nanoformulations, the dosage of therapeutic agents could be decreased and attain prolonged activity. Due to the co-delivery of therapeutic agents, the nanoformulations shows the synergistic effects in cancer cells which will significantly controls the aggressive tumors. The nanoformulation is non-immunogenic in C57/BL6 mice which indicate the future therapeutic application in cancer therapy.

We claim:

1. A nanoformulation for targeted treatment of cancer cells expressing HER2+ receptors and delivery of an anticancer drug to the cancer cells, the nanoformulation comprising:
   a. a plurality of gold nanoparticles (AuNP);
   b. a bi-functional engineered recombinant fusion protein TRAF(C);
   c. an anticancer drug; and
   d. erbB2 siRNA having a polynucleotide sequence set forth in SEQ ID NO: 6;
   wherein the bi-functional engineered recombinant fusion protein is conjugated to a surface of the gold nanoparticles (AuNP) using a reactive thiol moiety by introducing a C-terminal cysteine, and wherein a dose of the erbB2 siRNA in the nanoformulation is in the range of 0.1 to 0.25 mg/kg.

2. The nanoformulation of claim 1, wherein a size of the gold nanoparticles is in the range of 10-100 nm.

3. The nanoformulation of claim 1, wherein the anticancer drug is selected from the group consisting of doxorubicin, gemcitabine, cisplatin, and methotrexate.

4. The nanoformulation of claim 3, wherein the anticancer drug is doxorubicin.

5. The nanoformulation of claim 4, wherein a dose of doxorubicin is in the range of 0.1 to 2.5 mg/kg.

6. The nanoformulation of claim 1, wherein the cancer is selected from the group consisting of breast cancer, ovarian cancer, melanoma, glioma, and prostate cancer.

7. A pharmaceutical composition comprising a therapeutic amount of the nanoformulation of claim 1.

8. A method of treating cancer cells expressing HER2+ receptors, wherein the method comprises administering to a subject in need thereof a therapeutically effective amount of the nanoformulation of claim 1.

9. The method of treating cancer cells of claim 8, wherein the nanoformulation is administered by intraperitoneal, oral, intravenous, intramuscular, or subcutaneous route.

10. A process for preparation of the nanoformulation of claim 1, the process comprising:
   (i) conjugating freshly prepared AuNPs with recombinant fusion protein TRAF(C) to obtain a conjugate;
   (ii) incubating the conjugate obtained in (i) for 30 min at room temperature and constantly stirring to form an Au-TR complex;
   (iii) conjugating doxorubicin (DX) to the Au-TR complex obtained in (ii) and incubating for 30 mins at room temperature to obtain an intermediate conjugate;
   (iv) centrifuging the intermediate conjugate obtained in (iii) at 15,000 rpm for 45 min at 19-21° C. to form an Au-TR-DX complex;
   incubating the Au-TR-DX complex obtained in (iv) with a 5:1 mole ratio of siRNA for 30 minutes to obtain the nanoformulation.

* * * * *

SEQUENCE LISTING

```
<160> NUMBER OF SEQ ID NOS: 6

<210> SEQ ID NO 1
<211> LENGTH: 5369
<212> TYPE: DNA
<213> ORGANISM: Escherichia coli

<400> SEQUENCE: 1
atccggatat agttcctcct ttcagcaaaa aaccccctcaa gacccgttta gaggccccaa        60
ggggttatgc tagttattgc tcagcggtgg cagcagccaa ctcagcttcc tttcgggctt       120
tgttagcagc cggatctcag tggtggtggt ggtggtgctc gagtgcggcc gcaagcttgt       180
cgacggagct cgaattcgga tccgcgaccc atttgctgtc caccagtcat gctagccata       240
tggctgccgc gcggcaccag gccgctgctg tgatgatgat gatgatggct gctgcccatg       300
gtatatctcc ttcttaaagt taaacaaaat tatttctaga ggggaattgt tatccgctca       360
caattcccct atagtgagtc gtattaattt cgcgggatcg agatctcgat cctctacgcc       420
```

```
ggacgcatcg tggccggcat caccggcgcc acaggtgcgg ttgctggcgc ctatatcgcc    480
gacatcaccg atggggaaga tcgggctcgc cacttcgggc tcatgagcgc ttgtttcggc    540
gtgggtatgg tggcaggccc cgtggccggg ggactgttgg gcgccatctc cttgcatgca    600
ccattccttg cggcggcggt gctcaacggc ctcaacctac tactgggctg cttcctaatg    660
caggagtcgc ataagggaga gcgtcgagat cccggacacc atcgaatggc gcaaaacctt    720
tcgcggtatg gcatgatagc gcccggaaga gagtcaattc agggtggtga atgtgaaacc    780
agtaacgtta tacgatgtcg cagagtatgc cggtgtctct tatcagaccg tttcccgcgt    840
ggtgaaccag gccagccacg tttctgcgaa aacgcgggaa aaagtggaag cggcgatggc    900
ggagctgaat tacattccca accgcgtggc acaacaactg gcgggcaaac agtcgttgct    960
gattggcgtt gccacctcca gtctggccct gcacgcgccg tcgcaaattg tcgcggcgat   1020
taaatctcgc gccgatcaac tgggtgccag cgtggtggtg tcgatggtag aacgaagcgg   1080
cgtcgaagcc tgtaaagcgg cggtgcacaa tcttctcgcg caacgcgtca gtgggctgat   1140
cattaactat ccgctggatg accaggatgc cattgctgtg gaagctgcct gcactaatgt   1200
tccggcgtta tttcttgatg tctctgacca gacacccatc aacagtatta ttttctccca   1260
tgaagacggt acgcgactgg gcgtggagca tctggtcgca ttgggtcacc agcaaatcgc   1320
gctgttagcg ggcccattaa gttctgtctc ggcgcgtctg cgtctggctg gctggcataa   1380
atatctcact cgcaatcaaa ttcagccgat agcggaacgg gaaggcgact ggagtgccat   1440
gtccggtttt caacaaacca tgcaaatgct gaatgagggc atcgttccca ctgcgatgct   1500
ggttgccaac gatcagatgg cgctgggcgc aatgcgcgcc attaccgagt ccgggctgcg   1560
cgttggtgcg gatatctcgg tagtgggata cgacgatacc gaagacagct catgttatat   1620
cccgccgtta accaccatca aacaggattt tcgcctgctg gggcaaaacca gcgtggaccg   1680 cttgctgcaa ctctctcagg gccaggcggt gaagggcaat cagctgttgc ccgtctcact   1740
ggtgaaaaga aaaaccaccc tggcgcccaa tacgcaaacc gcctctcccc gcgcgttggc   1800
cgattcatta atgcagctgg cacgacaggt ttcccgactg gaaagcgggc agtgagcgca   1860
acgcaattaa tgtaagttag ctcactcatt aggcaccggg atctcgaccg atgcccttga   1920
gagccttcaa cccagtcagc tccttccggt gggcgcgggg catgactatc gtcgccgcac   1980
ttatgactgt cttctttatc atgcaactcg taggacaggt gccggcagcg ctctgggtca   2040
ttttcggcga ggaccgcttt cgctggagcg cgacgatgat cggcctgtcg cttgcggtat   2100
tcggaatctt gcacgccctc gctcaagcct tcgtcactgg tcccgccacc aaacgtttcg   2160
gcgagaagca ggccattatc gccggcatgg cggccccacg ggtgcgcatg atcgtgctcc   2220
tgtcgttgag gacccggcta ggctggcggg gttgccttac tggttagcag aatgaatcac   2280
cgatacgcga gcgaacgtga agcgactgct gctgcaaaac gtctgcgacc tgagcaacaa   2340
catgaatggt cttcggtttc cgtgtttcgt aaagtctgga acgcggaag tcagcgccct   2400 gcaccattat gttccggatc tgcatcgcag gatgctgctg ctaccctgt ggaacaccta   2460 catctgtatt aacgaagcgc tggcattgac cctgagtgat ttttctctgg tcccgccgca   2520
tccataccgc cagttgttta ccctcacaac gttccagtaa ccgggcatgt tcatcatcag   2580
taacccgtat cgtgagcatc ctctctcgtt tcatcggtat cattacccc atgaacagaa   2640 atccccctta cacggaggca tcagtgacca acaggaaaa aaccgccctt aacatggccc   2700
gctttatcag aagccagaca ttaacgcttc tggagaaact caacgagctg gacgcggatg   2760
aacaggcaga catctgtgaa tcgcttcacg accacgctga tgagctttac cgcagctgcc   2820
```

```
tcgcgcgttt cggtgatgac ggtgaaaacc tctgacacat gcagctcccg gagacggtca    2880
cagcttgtct gtaagcggat gccgggagca gacaagcccg tcagggcgcg tcagcgggtg    2940
ttggcgggtg tcggggcgca gccatgaccc agtcacgtag cgatagcgga gtgtatactg    3000
gcttaactat gcggcatcag agcagattgt actgagagtg caccatatat gcggtgtgaa    3060
ataccgcaca gatgcgtaag gagaaaatac cgcatcaggc gctcttccgc ttcctcgctc    3120
actgactcgc tgcgctcggt cgttcggctg cggcgagcgg tatcagctca ctcaaaggcg    3180
gtaatacggt tatccacaga atcaggggat aacgcaggaa agaacatgtg agcaaaaggc    3240
cagcaaaagg ccaggaaccg taaaaaggcc gcgttgctgg cgtttttcca taggctccgc    3300 cccctgacg agcatcacaa aaatcgacgc tcaagtcaga ggtggcgaaa cccgacagga    3360
ctataaagat accaggcgtt tccccctgga agctccctcg tgcgctctcc tgttccgacc    3420
ctgccgctta ccggatacct gtccgccttt ctcccttcgg aagcgtggc gctttctcat    3480 agctcacgct gtaggtatct cagttcggtg taggtcgttc gctccaagct gggctgtgtg    3540
cacgaacccc ccgttcagcc cgaccgctgc gccttatccg gtaactatcg tcttgagtcc    3600
aacccggtaa gacacgactt atcgccactg gcagcagcca ctggtaacag gattagcaga    3660
gcgaggtatg taggcggtgc tacagagttc ttgaagtggt ggcctaacta cggctacact    3720
agaaggacag tatttggtat ctgcgctctg ctgaagccag ttaccttcgg aaaaagagtt    3780
ggtagctctt gatccggcaa acaaaccacc gctggtagcg tggttttttt tgtttgcaag    3840
cagcagatta cgcgcagaaa aaaggatct caagaagatc ctttgatctt ttctacgggg    3900
tctgacgctc agtggaacga aaactcacgt taagggattt tggtcatgaa caataaaact    3960
gtctgcttac ataaacagta atacaagggg tgttatgagc catattcaac gggaaacgtc    4020
ttgctctagg ccgcgattaa attccaacat ggatgctgat ttatatgggt ataaatgggc    4080
tcgcgataat gtcgggcaat caggtgcgac aatctatcga ttgtatggga agcccgatgc    4140
gccagagttg tttctgaaac atggcaaagg tagcgttgcc aatgatgtta cagatgagat    4200
ggtcagacta aactggctga cggaatttat gcctcttccg accatcaagc atttatccg    4260 tactcctgat gatgcatggt tactcaccac tgcgatcccc gggaaaacag cattccaggt    4320
attagaagaa tatcctgatt caggtgaaaa tattgttgat gcgctggcag tgttcctgcg    4380
ccggttgcat tcgattcctg tttgtaattg tccttttaac agcgatcgcg tatttcgtct    4440
cgctcaggcg caatcacgaa tgaataacgg tttggttgat gcgagtgatt ttgatgacga    4500
gcgtaatggc tggcctgttg aacaagtctg gaaagaaatg cataaacttt tgccattctc    4560
accggattca gtcgtcactc atggtgattt ctcacttgat aaccttattt ttgacgaggg    4620
gaaattaata ggttgtattg atgttggacg agtcggaatc gcagaccgat accaggatct    4680
tgccatccta tggaactgcc tcggtgagtt ttctccttca ttacagaaac ggcttttca    4740 aaaatatggt attgataatc ctgatatgaa taaattgcag tttcatttga tgctcgatga    4800 gttttttctaa gaattaattc atgagcggat acatatttga atgtatttag aaaaataaac    4860
aaataggggt tccgcgcaca tttccccgaa aagtgccacc tgaaattgta acgttaata    4920 ttttgttaaa attcgcgtta aattttttgtt aaatcagctc attttttaac caataggccg    4980
aaatcggcaa aatcccttat aaatcaaaag aatagaccga gatagggttg agtgttgttc    5040
cagtttggaa caagagtcca ctattaaaga acgtggactc caacgtcaaa gggcgaaaaa    5100
ccgtctatca gggcgatggc ccactacgtg aaccatcacc ctaatcaagt ttttggggt    5160
```

```
cgaggtgccg taaagcacta atcggaacc ctaaagggag cccccgattt agagcttgac      5220
ggggaaagcc ggcgaacgtg gcgagaaagg aagggaagaa agcgaaagga gcgggcgcta      5280
gggcgctggc aagtgtagcg gtcacgctgc gcgtaaccac cacacccgcc gcgcttaatg      5340
cgccgctaca gggcgcgtcc cattcgcca                                       5369

<210> SEQ ID NO 2
<211> LENGTH: 1888
<212> TYPE: DNA
<213> ORGANISM: Homo sapiens

<400> SEQUENCE: 2
gcctctccag ctgcgacaca gatggcgcgc gggctcttgg gttctgtagt tttctcgcga       60
tccaaaaggc tccgtgccca agtgagtcct taccgcctcc ctaccagcg gcttcccctc      120 cgctagtacg catgtccaca gcttcacgga ccgggagaga gggggcgcgg aaggaaggag      180
gcgggacggt attacaaaca aaaaaatacg gccttctcga gaagcgacgg cggagggccc      240
gctcctccca gaaggcggtg cagcctgccc gggcgagcca cgcacgcaga gggttgtggg      300
gcggatagct cccctccaga tggaggctca cgaagtaggg tgggcggggg actccatatc      360
ccagcgtgcc ccgcggcggg ccctaccggc cgcgactccg ggcttggccc cggccctagc      420
tcgtcggctg tgtattgggg cgcgtggagg ctgcagtcac ggtggcgccc gcgggggacgg      480 aggagggaat gagtgaagag gagcaaggct ccggcactac cacgggctgc gggctgccta      540
gtatagagca aatgctggcc gccaacccag gcaagacccc gatcagcctt ctgcaggagt      600
atgggaccag aatagggaag acgcctgtgt acgaccttct caaagccgag ggccaagccc      660
accagcctaa tttcaccttc cgggtcaccg ttggcgacac cagctgcact ggtcagggcc      720
ccagcaagaa ggcagccaag cacaaggcag ctgaggtggc cctcaaacac ctcaaagggg      780
ggagcatgct ggagccggcc ctggaggaca gcagttcttt ttctccccta gactcttcac      840
tgcctgagga cattccggtt tttactgctg cagcagctgc tacccagtt ccatctgtag      900 tcctaaccag gagccccccc atggaactgc agccccctgt ctccctcag cagtctgagt      960 gcaacccgt tggtgctctg caggagctgg tggtgcagaa aggctggcgg ttgccggagt     1020
acacagtgac ccaggagtct gggccagccc accgcaaaga attcaccatg acctgtcgag     1080
tggagcgttt cattgagatt gggagtggca cttccaaaaa attggcaaag cggaatgcgg     1140
cggccaaaat gctgcttcga gtgcacacgg tgcctctgga tgcccgggat ggcaatgagg     1200
tggagcctga tgatgaccac ttctccattg gtgtgggctc ccgcctggat ggtcttcgaa     1260
accggggccc aggttgcacc tgggattctc tacgaaattc agtaggagag aagatcctgt     1320
ccctccgcag ttgctccctg gctccctgg gtgccctggg ccctgcctgc tgccgtgtcc     1380
tcagtgagct ctctgaggag caggcctttc acgtcagcta cctggatatt gaggagctga     1440
gcctgagtgg actctgccag tgcctggtgg aactgtccac ccagccggcc actgtgtgtc     1500
atggctctgc aaccaccagg gaggcagccc gtggtgaggc tgcccgccgt gcctgcagt     1560 acctcaagat catggcaggc agcaagtgaa gccccagctg gactcatgga tgtgcaccct     1620
ttgctccctg ctctttctgc ctctgggctc atgtatctgc gcagtctgg taccctctgt     1680 gggtgccatc tctacctctg acacagactg cctgccttga agctgagaag gcacagggca     1740
aggagccaag gaccacagag cctcagccag cccaggatcc gtcctcattt tattggtgat     1800
gatgaatggg aatgaaatca gggggctgtc tactagagcc tggaataaat atgctgcttt     1860
gtggattttt aaaaaaaaaa aaaaaaaa                                        1888
```

```
<210> SEQ ID NO 3
<211> LENGTH: 33
<212> TYPE: DNA
<213> ORGANISM: Escherichia coli

<400> SEQUENCE: 3 tttttcata tgggctcccc tcagcagtct gag                                    33

<210> SEQ ID NO 4
<211> LENGTH: 32
<212> TYPE: DNA
<213> ORGANISM: Escherichia coli
<220> FEATURE:
<221> NAME/KEY: misc_feature
<222> LOCATION: (31)..(31)
<223> OTHER INFORMATION: n is a, c, g, or t

<400> SEQUENCE: 4
gtggtgctcg agtcattagc atttcggcgc nt                                    32

<210> SEQ ID NO 5
<211> LENGTH: 1206
<212> TYPE: DNA
<213> ORGANISM: Escherichia coli

<400> SEQUENCE: 5
gttaaagagg aacaatttcc cctctagaat aattttgttt aactttaaga aggagatata       60
ccatgggcag cagccatcat aaacatcatc acagcagcgg cctggtgccg cgcggcagcc      120
atatgggctc ccctcagcag tctgagtgca accccgttgg tgctctgcag gagctggtgg      180
tgcagaaagg ctggcggttg ccggagtaca cagtgaccca ggagtctggg ccagcccacc      240
gcaaagaatt caccatgacc tgtcgagtgg agcgtttcat tgagattggg agtggcactt      300
ccaaaaaatt ggcaaagcgg aatgcggcgg ccaaaatgct gcttcgagtg cacacggtgc      360
ctctggatgc ccgggatggc ggcggaggtg gcgtggataa caaatttaac aaagaaatgc      420
gcaacgcgta ttgggaaatt gcgctgctgc cgaacctgaa caaccagcag aaacgcgcgt      480
ttattcgcag cctgtatgat gatccgagcc agagcgcgaa cctgctggcg gaagcgaaaa      540
aactgaacga tgcgcaggcg ccgaaatgct aatgactcga gcaccaccac caccaccact      600
gagatccggc tgctaacaaa gcccgaaagg aagctgagtt ggctgctgcc accgctgagc      660
aataactagc ataaccccct ggggcctcta acgggtctt gagggttt ttgctgaaag        720 gaggaactat atccggattg gcgaatggga cgcgccctgt agcggcgcat taagcgcggc      780
gggtgtggtg gttacgcgca gcgtgaccgc tacacttgcc agcgccctag cgcccgctcc      840
tttcgctttc ttcccttcct ttctcgccac gttcgccggc tttccccgtc aagctctaaa      900 tcggggctc cctttagggt tccgatttag tgctttacgg cacctcgacc ccaaaaaact      960
tgattagggg tgatggttca cgtagtgggc catcgccctg atagacggt ttttcgccct      1020 ttgacgttgg agtccacgtt ctttaatagt gactcttgtt ccaaactgga caaccctca     1080 accctatctc ggtctattct ttttgattta taggggattt ggcgattcgg cctattggtg     1140
aaaaatgagc tgattgacca agttaggcga attacaaaat taaacgctaa gttaggttgc     1200
cctttc                                                                1206

<210> SEQ ID NO 6
<211> LENGTH: 19
<212> TYPE: RNA
```

```
<213> ORGANISM: Artificial Sequence
<220> FEATURE:
<223> OTHER INFORMATION: siRNA for human ERBB2

<400> SEQUENCE: 6
agacgaagca uacgugaug                                                    19
```